US007615617B2

(12) United States Patent
Robinson et al.

(10) Patent No.: US 7,615,617 B2
(45) Date of Patent: Nov. 10, 2009

(54) USE OF HYDROSTATIC PRESSURE TO INHIBIT AND REVERSE PROTEIN AGGREGATION AND FACILITATE PROTEIN REFOLDING

(75) Inventors: Anne Skaja Robinson, Kennett Square, PA (US); Clifford R. Robinson, Kennett Square, PA (US); Debora Foguel, Copa Cabana (BR); Jerson Lima Silva, Copa Cabana (BR)

(73) Assignee: University of Delaware, Newark, DE (US)

( * ) Notice: Subject to any disclaimer, the term of this patent is extended or adjusted under 35 U.S.C. 154(b) by 460 days.

(21) Appl. No.: 10/673,000

(22) Filed: Sep. 26, 2003

(65) Prior Publication Data

US 2005/0020818 A1 Jan. 27, 2005

Related U.S. Application Data

(62) Division of application No. 09/695,762, filed on Oct. 25, 2000, now abandoned.

(60) Provisional application No. 60/161,035, filed on Oct. 25, 1999.

(51) Int. Cl.
*A23J 1/00* (2006.01)
*C07K 14/00* (2006.01)
(52) U.S. Cl. ...................... 530/412; 530/350
(58) Field of Classification Search .............. 435/3, 435/4; 436/2, 55, 148; 530/412, 350
See application file for complete search history.

(56) References Cited

U.S. PATENT DOCUMENTS 5,288,462 A 2/1994 Carter et al.
6,489,450 B2 * 12/2002 Randolph et al. ........... 530/427
6,635,469 B1 * 10/2003 Litt et al. .................. 435/287.1

FOREIGN PATENT DOCUMENTS

WO WO 02/062827 A2 8/2002

OTHER PUBLICATIONS

Lehninger et al., "Principles of Biochemistry with an Extended Discussion of Oxygen-Binding Proteins", 1993, Worth Publishers, Second Edition, p. 160.*
Paladini et al., "Pressure-induced reversible dissociation of enolase", Apr. 28, 1981, Biochemistry, vol. 20, No. 9, pp. 2587-2593.*
Panick et al., "Structural characterization of the pressure-denatured state and unfolding/refolding kinetics of staphylococcal nuclease by synchrotron small-angle X-ray scattering and Fourier-transform infrared spectroscopy", Jan. 16, 1998, Journal of Molecular Biology, vol. 275, Issue 2, pp. 389-402.*
Gorovits et al., "High Hydrostatic Pressure Can Reverse Aggregation of Protein Folding Intermediates and Facilitate Acquisition of Native Structure", Apr. 28, 1998, Biochemistry, vol. 37, No. 17, pp. 6132-6135.*

Lehninger et al., "Principles of Biochemistry with an Extended Discussion of Oxygen-Binding Proteins", 1993, Worth Publishers, Second Edition, p. 160.*
Foguel et al., 1999, Hydrostatic Pressure Rescues native protein form Aggregates, Biotechnology and Bioengineering, 63(5): 552-558.*
Silva et al., 1989, Anomalous Pressure Dissociation of Large Protien Aggregates, The Journal of Biological Chemistry, 264(27): 15863-15868.*
Bonafe et al., 1994, Intermediate States of Assembly in the Dissociation of Gastropod Hemocyanin by Hydrostatic Pressure, Biochemistry, 33: 2651-2660.*
Anne S. Robinson, Grant Application Abstract, Career: Characterization, Inhibition, and Reversal of Protein Aggregation, Jun. 1, 2000, Abstract Only.
Anne S. Robinson, Grant Application Abstract, Powre: Molecular Determinants and Inhibition of Protein Aggregation, Oct. 1, 1997, Abstract Only.
Anne S. Robinson, Oral Presentation, Engineering Approaches to Reversing Protein Aggregation, Mid-Atlantic Biochemical Engineering Consortium, Apr. 7, 2000, University of Delaware, Abstract, Abstract Only.
Anne S. Robinson, Poster Presentation, The Role of Cysteines and Disulfide Bonds in the Protein Folding of P22 Tailspike, Mid-Atlantic Biochemical Engineering Consortium, Apr. 7, 2000, University of Delaware, Abstract, Abstract Only.
Cleland, "Impact of Protein Folding on Biotechnology", Protein folding: In vivo and in vitro *American Chemical Society* (1993) 526: 1-21.
DeBernardez-Clark et al., "Inclusion Bodies and Recovery of Proteins from the Aggregated State", *Protein Refolding, American Chemical Society* (1991) 470: 1-20.
Foguel et al., "Characterization of a Partially Folded Monomer of the DNA-binding Domain of Human Papillomavirus E2 Protein Obtained at High Pressure", *J Biol Chem* (1998) 273(15): 9050-7.
Gorovits et al., "High Hydrostatic Pressure Can Reverse Aggregatin of Protein Folding Intermediates and Facilitate Acquisition of Native Structure", *Biochemistry* (1998) 37(17): 6132-5.
Jurkiewicz et al., "Inactivation of simian immunodeficiency virus by hydrostatic pressure", *Proc. Natl. Acad. Sci. USA* (1995) 92: 6935-7.
Robinson et al., "Hydrostatic and Osmotic Pressure as Tools to Study Macromolecular Recognition", *Methods in Enzymol* (1995) 259: 395-427.
Shigehisa et al., "Effects of high hydrostatic pressure on characteristics of pork slurries and inactivation of microorganisms associated with meat and meat products" *Int J Food Microiol* (1991) 12(2-3): 207-15.

(Continued)

*Primary Examiner*—Amber D. Steele
(74) *Attorney, Agent, or Firm*—RatnerPrestia

(57) ABSTRACT

A novel approach is described for reversing aggregation and increasing refolding by application of hydrostatic pressure. A protein of interest in an aggregated, or inclusion body, or other non-native or inactive state is subjected to high hydrostatic pressure. This treatment denatures the protein to states (or conformations) competant for refolding and results in increased formation of native protein once pressure is released. The technique can facilitate conversion non-native proteins, including inclusion bodies and aggregates to native proteins without addition of chaotropic agents, changes in buffer, or large-scale dilution of reagents required for traditional refolding methods.

6 Claims, 8 Drawing Sheets

OTHER PUBLICATIONS

Silva et al., "Effects of hydrostatic pressure on a membrane-enveloped virus: High Immunogenicity of the pressure-inactivated virus", *J. Virol.* (1992) 66: 2111-7.

Silva et al., "Pressure Stability of Proteins", *Annu. Rev. Phys. Chem.* (1993) 44: 89-113.

Silva et al., "The use of hydrostatic pressure as a tool to study viruses and other macromolecular assemblages", *Current Opinion in Structural Biology* (1996) 6(2): 166-75.

Tauscher, "Pasteurization of food by hydrostatic high pressure: chemical aspects" *Z Lebensm Unters Forsch* (1995) 200(1): 3-13.

Gorovits et al., "Rhodanese folding is controlled by the partitioning of its folding intermediates", *Biochimica et Biophysica Acta 1382* (1998) 120-128.

Webb et al., "Stability of Subtilisin and Lysozyme under High Hydrostatic Pressure", *American Chemical Society and American Institute of Chemical Engineers* (2000) A-G.

Silva et al., "Dissociation of a native dimer to a molten globule monomer. Effects of pressure and dilution on the association equilibrium of arc repressor", *J Mol Biol.* (1992) 223(2): 545-55.

Pontes et al., "Pressure Inactivation of Animal Viruses: Potential Biotechnological Applications", *High Pressure Research in the Biosciences and Biotechnology,* K. Heremans (Ed.) Leuven University Press, Leuven, Belgium, 1997.

Smelt et al., "Inactivation Kinetics of Microorganisms by High Pressure", *Pressure Research in the Biosciences and Biotechnology*, K. Heremans (Ed.) Leuven University Press, Leuven, Belgium, 1997.

Patterson et al., "The Effect of High Hydrostatic Pressure Treatment on Micro-organisms in Foods", *Pressure Research in the Biosciences and Biotechnology*, K. Heremans (Ed.) Leuven University Press, Leuven, Belgium, 1997.

Foguel et al., Hydrostatic Pressure Rescues Native Protein from Aggregates, *Biotechnology and Bioengineering* (1999) 63(5):552-558.

* cited by examiner

USE OF HYDROSTATIC PRESSURE TO INHIBIT AND REVERSE PROTEIN AGGREGATION AND FACILITATE PROTEIN REFOLDING

This application is a division of U.S. application Ser. No. 09/695,762, filed Oct. 25, 2000 now abandoned, which claims the benefit of U.S. Provisional Application No. 60/161,035, filed Oct. 25, 1999.

This work was supported in part by grants provided by the National Science Foundation (BES-9720570) and the National Institutes of Health (GM61727, GM17538). The government has certain rights in this invention.

FIELD OF THE INVENTION

The invention relates to methods for the recovery of protein in its native conformation from inclusion bodies and other aggregated protein samples, particularly through the application of high hydrostatic pressure.

BACKGROUND OF THE INVENTION

Protein aggregation and misfolding play major roles in protein production in the biotechnology industry, in limiting the biochemical study of proteins, and in the onset of pathogenesis in human disease. The native, correctly folded state is necessary for a protein's biological function and recognition by other molecules; misfolding and misassembly lead to significant loss of biological activity. Because the mechanism that drives aggregation is poorly understood it represents a challenge to industrial, academic, and medical research scientists.

Aggregation can occur by many distinct mechanisms (De Bernardez Clark, 1998). One such mechanism is formation of intermolecular disulfide bonds (e.g., Stoyan et al., 1993). Currently, refolding of proteins that have aggregated by incorrect disulfide bonding has been achieved by addition of oxidants or redox buffers (Builder et al., 1997; De Bernardez-Clark and Georgiou, 1991; Rudolph and Lilie, 1996). However, in many cases, other mechanisms predominate. For example, the aggregation events that result in Alzheimer s disease and prion diseases such as Creutzfeldt—Jacob's disease and bovine spongiform encephalopathy are believed to occur by noncovalent association of β-strands (Bychkova and Ptitsyn, 1995; Jarrett et al., 1993; Thomas 1992, 1995). Aggregation of tailspike protein is also believed to result from specific association of partially folded chains, possibly by misalignment of the β-strands (Speed et al., 1996).

Current methods for refolding proteins from non-covalent aggregates and inclusion bodies typically require that the proteins first be solubilized and nearly completely unfolded, typically through the use of strong chaotropic agents, such as guanidine chloride or urea, and reducing agents (Cleland, 1993). The proteins are then refolded by removal of the denaturant.

Aggregation is favored at higher protein concentrations. Consequently, removal of the denaturant frequently requires large dilution and therefore large working volumes. Low refolding yields are therefore common, due to the loss of protein during refolding and subsequent concentration (De Bernardez-Clark and Georgiou, 1991). Yield of protein in its native conformation upon renaturation is often low, regardless of refolding conditions.

To help prevent aggregation, refolding is often performed stepwise, using a series of gradual buffer changes, which decrease the concentration of a chaotropic denaturing agent. A second existing method to inhibit aggregation during refolding is to elevate, then slowly decrease temperature. Temperature control is also used to disfavor aggregation. Both of these processes are slow, labor intensive, costly and inefficient.

SUMMARY OF THE INVENTION

Production of recombinant proteins for industrial, research and medical applications is often severely limited by aggregation of the proteins, either in vivo during expression, or in vitro during purification or use. It has been discovered that by application of hydrostatic pressure, protein aggregation can be inhibited or reversed. It is effective both in preventing aggregation during refolding and in reversing aggregation which has already taken place. After pressure is released, dissociated aggregates refold to form biologically active protein with native characteristics. A surprising result of this process is that it substantially increases the level of refolded protein, compared to that recoverable by traditional methods for protein refolding.

An additional benefit of the present invention is that the use of the present invention substantially or even entirely obviates the need for urea or other denaturants. Without the necessity for denaturants or other undesirable additives, there is no need to change buffers or dilute protein in order to produce native proteins. Thus, the present invention supplies a cost-effective method that is readily suitable for industrial application, easy to scale up and straightforward to optimize for each desired protein.

Accordingly, certain embodiments of the present invention provide a method for recovering native protein from inclusion bodies by obtaining a sample having at least one inclusion body, where the inclusion body contains denatured protein, subjecting the sample to high hydrostatic pressure, where the high hydrostatic pressure unfolds the denatured protein, and returning the sample to ambient pressure so as to allow the unfolded protein to refold, thereby recovering native protein from the inclusion body. According to certain preferred embodiments, the high hydrostatic pressure is from about 1 to about 3.5 kbar or about 2.5 kbar.

According to certain embodiments, the sample is substantially free of a denaturing agent selected from the group consisting of guanidine hydrochloride, guanidine thiocyanate, sodium dodecyl sulfate (SDS), and Urea. Additionally, according to certain embodiments the sample is substantially free of sodium dodecyl sulfate (SDS).

The invention also provides embodiments of the above-described methods, where the protein is allowed to refold in the presence of a chaparone or isomerase. Similarly, the invention also provides embodiments where the protein is unfolded in the presence of a reducing agent. The present invention also provides certain embodiments where the sample is obtained from a cell lysed by hydrostatic pressure.

The present invention also provides a method for determining the optimal hydrostatic pressure to a recover native protein of interest from a protein aggregate by obtaining a sample having a protein aggregate, where the protein aggregate contains a non-native protein of interest, subjecting the sample to high hydrostatic pressure, where the high hydrostatic pressure unfolds the non-native protein, returning the sample to ambient pressure, so as to allow the unfolded protein to refold, and assaying for the amount or concentration of the native protein of interest in the sample each tested hydrostatic pressure.

The present invention also provides a method to inhibit or reverse protein aggregation by subjecting a sample to high hydrostatic pressure, where the sample contains a protein aggregate, so as to substantially unfold the protein of the protein aggregate, and returning the sample to ambient pressure so as to allow the unfolded protein to refold, thereby recovering native protein from the protein aggregate. In accordance with certain embodiment of such methods, the high hydrostatic pressure is from preferably about 1 to about 3.5 kbar or about 2.5 kbar.

The invention also provides embodiment of such methods where the sample is substantially free of a denaturing agent selected from the group consisting of guanidine hydrochloride, guanidine thiocyanate, sodium dodecyl sulfate (SDS), and Urea. Similarly the present invention provides embodiments of such methods where the sample is substantially free of sodium dodecyl sulfate (SDS).

The invention also provides embodiment of such methods where the protein is allowed to refold in the presence of a chaparone or isomerase. Similarly, the invention provides embodiments of such methods where the denatured protein is unfolded in the presence of a reducing agent. The present invention also provides embodiments of such methods where the sample comprises a cell, the cell being lysed by high hydrostatic pressure.

The present invention also provides a method for increasing the yield of native protein from a cell expressing a recombinant protein by preparing a lysate from a cell expressing a recombinant gene, subjecting at least a portion of the lysate to high hydrostatic pressure, where the high hydrostatic pressure unfolds the denatured protein, and returning the portion of the lysate to ambient pressure so as to allow the unfolded protein to refold, thereby increasing the yield of native protein from the cell expressing a recombinant protein.

In accordance with such methods, the present invention provides certain embodiments where a portion of the lysate comprises a cytosolic fraction, a membrane fraction or inclusion bodies. The present invention also provides certain embodiments of such methods where the high hydrostatic pressure is from about 1 to about 3.5 kbar or about 2.5 kbar.

According to certain embodiments of these methods the sample is substantially free of a denaturing agent selected from the group consisting of guanidine hydrochloride, guanidine thiocyanate, sodium dodecyl sulfate (SDS), and Urea. Similarly, according to certain embodiments of these methods, the sample is substantially free of sodium dodecyl sulfate (SDS).

The invention also provides embodiments of such methods where the protein is allowed to refold in the presence of a chaparone or isomerase. The invention also provides embodiments of such methods where the denatured protein is unfolded in the presence of a reducing agent.

DETAILED DESCRIPTION OF THE INVENTION

Figure 1:
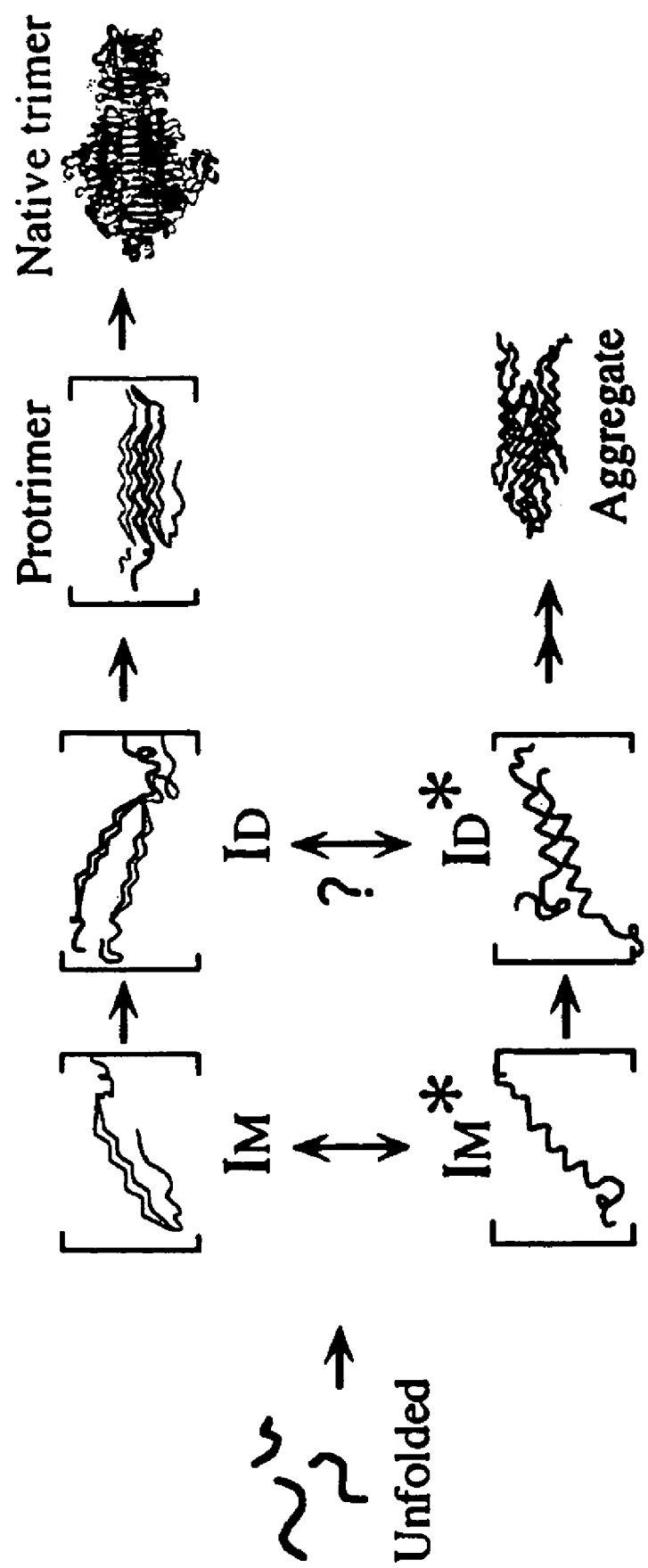
FIG. 1 is a schematic diagram of the P22 tailspike protein aggregation and assembly pathways.

It has been discovered that by application of hydrostatic pressure, protein aggregation can be inhibited or reversed. High hydrostatic pressure is effective both. in preventing aggregation during refolding and in reversing aggregation which has already taken place. After pressure is released, dissociated aggregates refold to form biologically active protein with native characteristics. A surprising result of this process is that it can substantially increase the recovery level of refolded protein, compared to that recoverable by traditional methods for protein refolding. The partially unfolded intermediates appear to preferably refold into the conformation of the native protein, rather than merely re-aggregating upon release of pressure.

One benefit of the present invention is that the use of the present invention can substantially or even entirely remove the need for urea or other denaturants. Without the necessity for denaturants or other undesirable additives, there is no need to change buffers or dilute protein in order to produce native proteins. Thus, the present invention supplies a cost-effective method that is readily suitable for industrial application, easy to scale up and straightforward to optimize for each desired protein.

The term "protein aggregate" is used herein, in accordance with its ordinary meaning in the art. Specifically, the term protein aggregate is not intended to include the normal association between subunits of a native multi-subunit protein complex or the normal association of capsomeres in a native viral particle.

The term "inclusion body" is used herein, in accordance with its ordinary meaning in the art, to include a protein aggregate produced inside a cell. The term inclusion body does not solely refer to the intracellular protein aggregate when located within the intracellular milieu. The term may, for example, also refer to the intracellularly-produced protein aggregate after it has been isolated from the cell.

Prior to the present invention, hydrostatic pressure was shown to dissociate oligomeric proteins and other-macromolecular complexes without denaturing the secondary and tertiary structure of the subunits (Robinson and Sligar, 1995; Silva et al., 1996). Elevated hydrostatic pressure favors the state of lowest total volume—for most macromolecular assemblages this is the dissociated state (Silva and Weber, 1993).

Hydrostatic pressure was also shown to produce partially folded protein chains under equilibrium conditions (Foguel et al., J. Biol. Chem. 273:9050-9057 (1998); Silva et al. Curr. Opin. Struct. Biol. 6:166-175 (1996); Silva et al., J. Molec. Biol. 223:545-555 (1992). It was also demonstrated that proteins undergo reversible folding/unfolding transitions when subjected to hydrostatic pressures. Quaternary structures of oligomeric protein assemblies typically dissociate to monomeric subunits between 1 and 3 kbar. At room temperature, secondary and tertiary structures of proteins typically do not denature until pressures above 5 kbar (Robinson and Sligar, Meth. Enzymol. 259:395-427 (1995); Silva and Weber, Annu. Rev. Phys. Chem. 44:89-113 (1993)).

Hydrostatic pressure has been used in food preparation, particularly for sterilization purposes. (Heremans, 1997). Food pasteurized by hydrostatic pressure is being marketed worldwide. Shigehisa et al., Int. J. Food Microbiol. 12:207-215 (1991); Tauscher, Z Lebensm Unters Farsch 200:3-13 (1995); U.S. Pat. No. 5,288,462.

Hydrostatic pressure is known to inactivate viruses and has been evaluated with a view toward two potential applications, vaccine development and virus sterilization (Jurkiewicz et al., Proc. Natl. Acad. Sci. USA 92:6935-6937(1995); Pontes et al., Pressure inactivation of animal viruses: Potential biotechnological applications. In: *High-Pressure Research in the Biosciences and Biotechnology*. Heremans K, editor., Leuyen: Leuven University Press. p 91-94 (1997); Silva et al., J. Virol. 66:2111-2117 (1992).

Recently, it was shown that under conditions of high hydrostatic pressure (2 kbar), aggregation of rhodonase proceeds more slowly than at ambient pressure (Gorovits and Horowitz, Biochemistry 37:6132-6135 (1998)). It was also shown that a combination of hydrostatic pressure and 4 M urea can disrupt small, early rhodonase aggregation intermediates, until pressure is released. The effect was transitory and aggregation resumed when pressure was released. Hydrostatic pressure was also seen to allow improved recovery of native protein when, prior to substantial aggregation of the sample, denatured rhodanase was allowed refold under 2 kbar of hydrostatic pressure.

Until the present invention, however, high hydrostatic pressure has not been shown to reverse or inhibit protein aggregation so as to allow recovery of native protein, particularly in the substantial absence of denaturing agents such as urea. Furthermore, the art has not suggested that high hydrostatic pressure could be suitably applied to the recovery of protein from inclusion bodies. In fact, it has been theorized that protein aggregates, particularly those formed as inclusion bodies in vivo are simply jumbled arrays of essentially unfolded chains (Gorovits and Horowitz, 1998). According to such reasoning, high hydrostatic pressure would actually be expected to increase aggregation, because hydrostatic pressure favors denatured, dissociated states. Thus, the relevant art taught away from the present invention.

Reversal of protein aggregation by the present invention is believed to be somewhat analogous to pressure dissociation of oligomeric proteins. The chains that are dissociated by pressure are competent for rapid productive folding, perhaps because the secondary and tertiary structure is preserved. The pressure-sensitive interfaces of aggregates are likely to be well-packed and solvent-excluded, suggesting that aggregation involves specific protein-protein interactions.

In accordance with the present invention, a sample containing a protein of interest is subjected to high hydrostatic pressure. Preferably, the hydrostatic pressure is between about 0.5 kbar and 10 kbar, preferably about 1 kbar to about 3.5 kbar, most preferably about 2 to 3 kbar.

For inhibition of aggregation, denatured protein samples are typically shifted to folding conditions (typically by a change in buffer conditions or temperature), to initiate refolding. Preferably, hydrostatic pressure is immediately applied. After refolding is complete, pressure is restored to ambient levels.

For reversal of aggregation, protein aggregates are placed in a high pressure vessel and hydrostatic pressure is applied. The samples are incubated at elevated hydrostatic pressure and then returned to ambient pressure. Protein aggregates are substantially reduced, and folded protein is produced. Both methods can be performed at high protein concentrations (a condition which often predominantly favors aggregation).

Curiously, the yield of protein having its native conformation is frequently higher from more highly aggregated samples. Thus, in accordance with those methods of the present invention in which the desired protein is denatured prior to application of high hydrostatic pressure, the sample is preferably allowed to undergo significant aggregation. Preferably, the sample is allowed to aggregate for at least 30 minutes, more preferably the sample is allowed to aggregate for at least 60 minutes or at least 120 minutes prior to the application of high hydrostatic pressure.

Similarly, one advantage of the present invention, is that it allows refolding at higher protein concentrations. Higher protein concentrations typically favor protein aggregation in vitro and the formation of inclusion bodies, in vivo. Particularly where the desired protein is an oligomeric or multi-subunit protein, protein concentration can be a crucial parameter (De Bernardez Clark, 1998). As noted, the present invention is particularly suited for recovering native protein from inclusion bodies and other highly aggregated protein samples. Thus, in accordance with the present invention, at least 50%, preferably at least 70%, and more preferably at least 90% of the desired protein is aggregated prior to the application of high hydrostatic pressure.

The methods of the present invention are applicable to any protein. Thus, the protein of interest may be a single subunit protein. Alternatively, the protein of interest may be a multi-subunit protein. Essentially, any protein that can have a misalignment of structural elements may be suitably used in accordance with the methods of the present invention. Examples of such suitable proteins include proteins that have helices that pack together, as in four-helix bundle proteins (such as certain cytochromes), multi-pass membrane helical proteins (including 7-helix transmembrane receptors, such as rhodopsin and G-coupled coupled protein receptors), or β-sheet membrane proteins (such as porins). Other examples of proteins suitable for the methods of the present invention, include those that have β-sheet structures, such as Alzheimer's peptides or antibodies.

Assays for monitoring the native conformation of a protein will of course vary with the particular protein of interest. For example, antibodies specific for the native or denatured conformation of a protein may be suitably used to identify protein conformation. In the case of enzymes, suitable assays for the particular enzymatic activity may be suitably used in accordance with the methods of the invention. The particular assay will be guided by the particular protein. The present invention is not intended to be limited to any particular assay methodology. Suitable assays for the presence and/or concentration of conformation of the protein will be apparent to one of ordinary skill in the art.

According to certain methods of the present invention, the protein of interest may contain post-translational modifications, such as disulfide bonds. In such cases, the yield of native protein may be increased, for example, by inclusion of a suitable reducing agent such as β-ME. Other suitable reducing agents are known to those of ordinary skill in the art.

In accordance with certain methods of the present invention, refolding of the protein of interest may also be more efficient where refolding is accomplished in the presence of chaperones (such as GroEL or BiP) or isomerases (such as protein disulfide isomerase for disulfide bond rearrangement). Proteins having post-translational modifications are examples of proteins particularly suited to such methods. In accordance with the methods of the present invention, the chaperones or isomerases may either be present in the sample when subjected to high hydrostatic pressure or be added to the sample as the pressure is being released or following release of the pressure.

Inclusion bodies frequently result from the over-expression of a recombinant gene in a host cell. Inclusion bodies may, however, result from normal cellular processes that result in the accumulation of an intracellular protein aggregate. The present invention is particularly well suited for recovering native protein from inclusion bodies containing a protein of interest. In accordance with the present invention, the inclusion bodies may be from either eukaryotic or prokaryotic cells such as E. coli containing a recombinant expression vector or insect cells expressing a gene from a recombinant baculovirus expression vector.

High hydrostatic pressure may be used directly to lyse cells containing a protein of interest. According to certain preferred methods of the present invention, high hydrostatic pressure is utilized to both lyse cells containing a protein of interest and to facilitate recovery of the protein of interest in its native form. According to certain preferred embodiments, prior to subjecting the cells to high hydrostatic pressure, the cells are suspended in a suitable buffer. The cells are then subjected to high hydrostatic pressure, which causes the cells to lyse into the suspension buffer. Suitable buffers will of course vary with the individual protein of interest. In certain instances, the presence modest amounts of SDS, protease inhibitors or chaotropic agents may facilitate the methods of the present invention.

As high hydrostatic pressure can be used to assist or cause the lysis of cells in a sample, according to certain preferred embodiments of the present invention, a cell lysate suitable for the methods of the present invention may be produced without the use of harsh lysis solutions. One advantage of the present invention, therefore, is in reducing the need for subsequent desalting and/or purification steps to remove such solutions. Preparation of native protein is thereby substantially simplified.

The present invention is not limited to any particular apparatus for generating high hydrostatic pressure. In general, any device capable of subjecting the samples of the present invention to hydrostatic pressure sufficient for the methods of the present invention is suitable for the purposes of invention. For example, suitable devices are disclosed in the references cited herein. Other suitable devices for generating high hydrostatic pressure are known to those of ordinary skill in the art.

Typically, the protein of interest is subjected to high hydrostatic pressure at room temperature: Generally, however, protein unfolding can occur at lower pressures when at reduced temperatures. Reduced temperatures are particularly preferred in those embodiments where the protein of interest is particularly prone to aggregation. Thus, in accordance with certain embodiments of the present invention, the protein of interest is subjected to high hydrostatic pressure at reduced or elevated temperatures. Generally, such temperatures will fall between about −20° C. and about 50° C., preferably between about 0° C. and about 40° C. About 0° C., about 20° C. and about 37° C. are particularly preferred temperatures for the methods of the present invention. Similar temperatures are preferred temperatures for the remaining steps of the methods of the present invention. It may, however, be desirable for different steps to occur at different temperatures as, for example, aggregation at 0° C., administration of pressure at room temperature and return to atmospheric pressure at room temperature.

The tailspike protein of P22 bacteriophage is an excellent model system for aggregation because the structure is known, the folding and aggregation pathways are well characterized, and aggregation of tailspike chains occurs by specific interactions. The tailspike protein is a homotrimer of 666 residues per monomer chain (Sauer et al., Biochemistry 21:5811-5815 (1982)). The main body of each subunit of the trimer, residues 143-535, is a long 13-coil made of 13 complete turns (Steinbacher et al., Science 265:383-386 (1994)). The three chains then twist around each other to form three intertwined β-sheets comprising residues 536-619 (the "tail" region), where each sheet contains β-strands from all three subunits. The native tailspike trimer is thermostable ($t_m$=88° C.), and resistant to SDS and proteolysis. No covalent linkages exist in the native state of tailspike, and it is thought that the intertwined β-sheet plays a major role in stabilizing the tailspike trimer.

Tailspike protein is both a structural and functional. component of the P22 bacteriophage. Tailspike binds to the 0-antigen on the outer membrane lipopolysaccharide of Salmonella species and facilitates infection through hydrolysis of. the x(1-3)-glycosidic linkages (Iwashita and Kanegasaki, Eur. J. Biochem. 65:87-94 (1976)). This activity can be assayed for in vitro by incubating purified tailspike with tail-free viral heads, and measuring the "tailing" level by the formation of infectious particles (Berget and Poteete, J. Virol. 34:234-243 (1980)). The "tailing" ability serves as a functional assay for folded protein, whereas formation of native-like tertiary structure can be monitored by changes in SDS resistance and intrinsic fluorescence.

A number of intermediates along the in vivo and in vitro folding and aggregation pathways for P22 tailspike have been identified through native and denaturing gel electro-phoresis (FIG. 1) (Fuchs et al., Biochemistry 30:6598-6604 (1991); Goldenberg et al., J. Biol. Chem. 257:7864-7871 (1982); Goldenberg and King, Proc. Natl. Acad. Sci. USA 80:7060-7064 (1982); Haase-Pettingell and King, J. Biol. Chem. 263: 4977-4983 (1988); Robinson and King, Nature. Struct. Biol. 4:450-455 (1997); Seckler et al., J. Biol. Chem. 264:11750-11753 (1989); Speed et al., Prot. Sci. 4:900-908 (1995). Folding intermediates of tailspike are thermolabile and aggregate under physiological conditions in the host (Goldenberg et al., Proc. Natl. Acad. Sci. USA 80:7060-7064 (1983); Haase-Pettingell and King, J. Biol. Chem. 263:4977-4983 (1988)). A late trimeric intermediate, "protrimer," lacks the SDS resistance and thermal stability of the native proteins (Goldenberg et al, Proc. Natl. Acad. Sci. USA 79:3403-3407 (1982); Goldenberg and King, Proc. Natl. Acad. Sci. USA 79:3403-3407

(1982)). Although early folding intermediates are susceptible to aggregation, the propensity to aggregate is diminished once protrimer is formed. The presence of transient disulfide bonds in the protrimer intermediate may help promote folding and chain association of tailspike protein (Robinson and King, Nature Struct. Biol. 4:450-455 (1997)).

Aggregation of tailspike in vitro is not limited to sequential addition of monomers. Association can occur between subunit assemblies of any size—dimers can associate with monomers, dimers, trimers, tetramers, etc. (Speed et al., Prot. Sci. 4:900-908 (1995)). Aggregation does not occur by covalent association of the chains, as the addition of SDS in the absence of reducing agents dissociates aggregates into monomeric subunits (Robinson and King, 1997; Speed et al., 1995). In general, aggregation involves specific interactions between chains, since mixing of denatured tailspike protein with other aggregation-competent proteins (P22 coat protein, carbonic anhydrase) does not yield mixed aggregate species (Speed et al., Nature Biotechnol. 14:1283-1287 (1996)). In vitro, the extent of aggregation is dependent on both the protein and urea concentrations present in the refolding buffer.

Each reference cited in the present specification is hereby incorporated by reference in its entirety. The following examples are provided for illustrative purposes only, and are not intended to limit the scope of the invention disclosed herein.

EXAMPLES

Example 1

Aggregation Reactions Can Be Monitored by HPLC

Tailspike Protein Production: Tailspike protein is produced by infecting *Salmonella typhimurium* strain 7136 with phage P22 (Winston et al., J. Bacteriol. 137:433-439 (1979). Purification and $^{14}C$ metabolic labeling for radioactive protein is performed essentially as described in Robinson and King, Nature Struct. Biol. 4:450-455 (1997). Tailspike appears as a single band on both Coomasie- and silver-stained SDS gels. The tailspike protein is stored as an ammonium sulfate precipitate at 4° C., then dialyzed against 50 mM Tris-HCl (pH 7.0) and 1 mM EDTA just prior to use.

In Vitro Aggregation Reactions: Native tailspike protein is denatured for approximately 60 min in 7 M urea, 50 mM Tris-HCl (pH 3). The aggregation reaction is initiated by rapid dilution (12.5-fold) with 50 mM Tris-HCl (1 mM EDTA) at pH 7.6 to a final protein concentration of 100 μg/mL protein at 20° C. and 0.6 M urea. At 100 μ/mnL, greater than 90% of the tailspike will form aggregates. To monitor the extent of aggregation, 50 μL aliquots of the sample are taken at various time points and rapidly transferred to tubes containing 25 μL of 3× sample buffer (15 mM Tris-HCl , pH 6.8, 120 mM glycine, 50% glycerol, bromophenol blue), preincubated to 0° C. in an ice-water bath. These aliquots are then analyzed by electrophoresis. For HPLC analysis, 100 μL aliquots are removed, placed in an ice-water bath, and promptly injected into the HPLC.

Gel Electrophoresis: Nondenaturing polyacrylamide gel electrophoresis is performed using a discontinuous buffer system (Davis, 1964; Ornstein, 1964). The resolving gel contains 0.37 M TrisHCl (pH 8.0) with 3.8 mM TEMED, 3.0 mM ammonium persulfate, and 7.5% acrylamide. The stacking gel contains 70 mM Tris-HCl (pH 6.7) with 4.3% acrylamide, 7.5 mM TEMED, and 2.5 mM ammonium persulfate; The gels are run at constant current (10 mA/gel) for approximately 4 hours at 4° C. and then silver-stained. Quantitation of protein in different intermediates is determined by phosphorimaging of dried gels. In the native gels, the amount of aggregated protein is determined by adding the intensities of all aggregation intermediates in the resolving gel and large aggregates, which accumulate at the top of the stacking gel.

High-Performance Liquid Chromatography: High performance liquid chromatography (HPLC) is carried out in a Shimadsu system using a prepacked TSK3000 column. No precolumn is used in order to decrease the possibility of filtering out large, but soluble, aggregates. The system is equilibrated with 25 mM Tris-acetate (pH 7.0) in the presence of 0.5 M urea at a flow rate of 1.0 mL/min. Urea is included to decrease the propensity of partially folded proteins to stick to the column matrix. Sample elution is monitored by absorption at 280 nm and tryptophan emission at 340 nm (excitation at 280 nm). The column and buffer temperature are maintained at 0° C.

Figure 2:
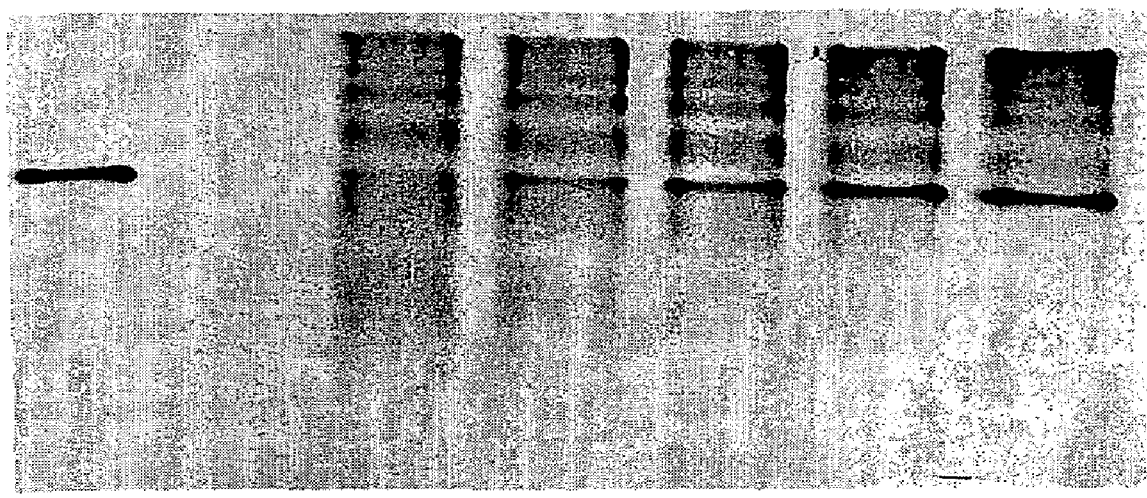
FIG. 2 is a diagram of a non-denaturing gel of C14-labelled P22 tailspike protein samples. Samples are denatured and allowed to aggregate for 2, 5, 10, 30 and 120 minutes.

Results: In the P22 tailspike system, folding and aggregation intermediates have been separated and visualized using native gel electrophoresis (Goldenberg et al., 1982; Robinson and King, 1997; Speed et al., 1995). King and colleagues assigned aggregation oligomerization states to native gel mobilities using Ferguson analysis (Speed et al., 1995). A time course for aggregation can be visualized and quantitated with native gel electrophoresis by using 14C-labeled tailspike (FIG. 2). Early timepoints (2 mm, 5 mm) show monomer, dimer, and higher order aggregate species. Later timepoints (30 mm, 2 h) show formation of some native trimer; however, higher order aggregation intermediates are the predominant species under the conditions of this experiment.

An HPLC assay, using size-exclusion HPLC (TSK3000 column, Supelco) is used to identify and quantitate aggregation intermediates rapidly. The column and buffer are kept at 0° C. in all of the experiments described here, to avoid additional association of tailspike chains inside the column during the run.

Using purified tailspike, the elution profiles of the native trimer and the denatured monomers are monitored by measuring absorption at 280 nm and fluorescence emission at 340 nm. The monomer and trimer both resolve as single peaks (data not shown). The trimer elutes as a uniform peak at 6.7 mm, and the monomer elutes at 7.6 mm.

Figure 3:
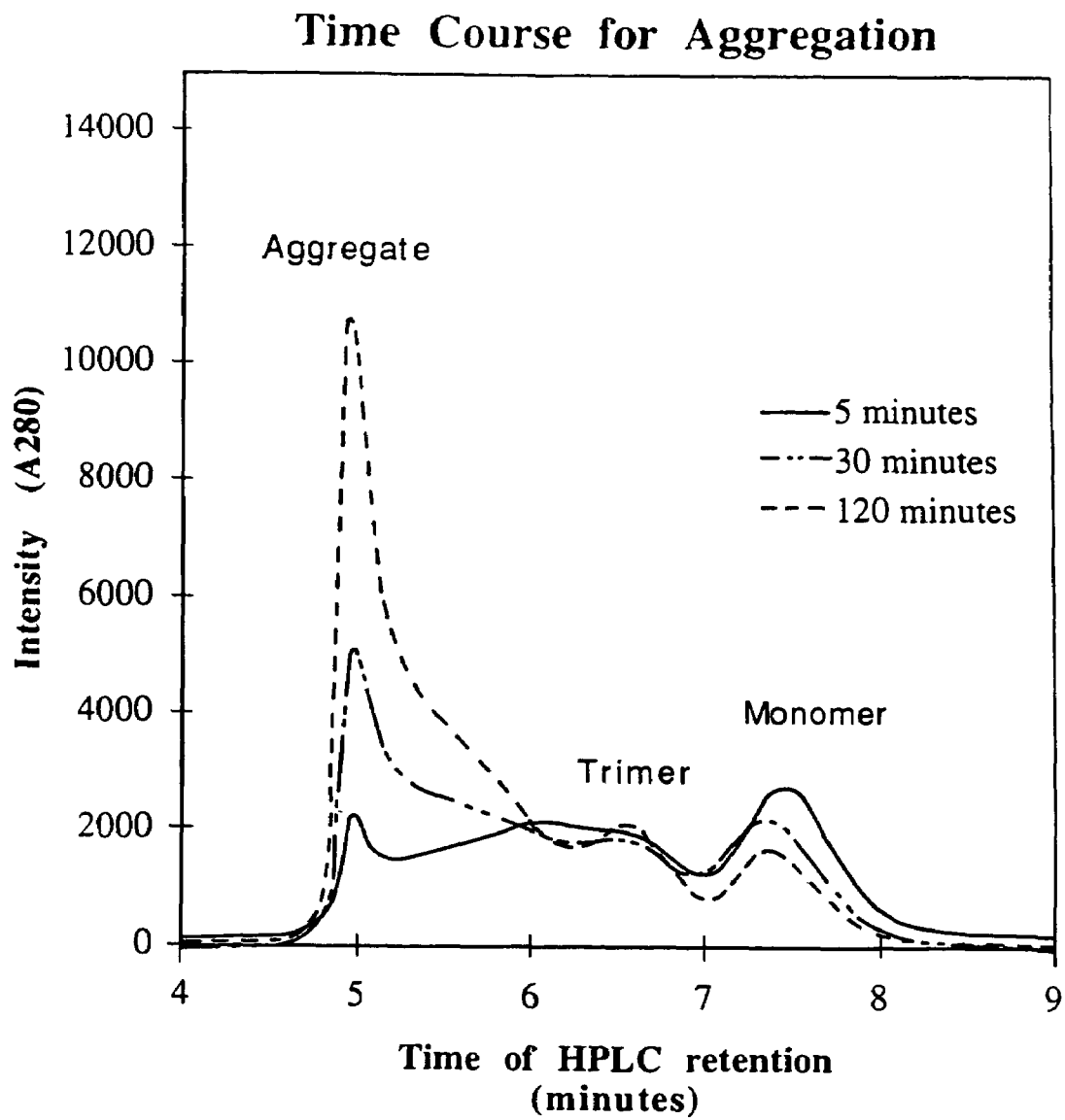
FIG. 3 is a graph showing that tailspike aggregation intermediates can be identified and quantitated by size-exclusion HPLC. Tailspike is denatured and allowed to aggregate for 5, 30 and 120 minutes. At the indicated times, samples are removed and injected into a TSK 3000 column. Peaks are detected by absorbance at 280 nm. The amounts of aggregate, trimer and monomer present in samples are shown.

To demonstrate that HPLC can be used as a probe for aggregation intermediates, tailspike is denatured, then rapidly diluted into refolding buffer. After the onset of aggregation, aliquots are removed at designated times and injected in the HPLC (FIG. 3). Three distinct peaks elute at 5.0, 6.6, and 7.5 mm after injection and a broad shoulder appears at 5.2 to 6.0 mm. Peaks are collected and analyzed by native gel electrophoresis, which allows identification of the peaks as follows: 5.0 mm, large aggregates; 6.6 mm trimer; 7.5 mm, monoimer (not shown). Monomer and trimer elute at the same times as purified tailspike samples, confirming the reproducibility of the technique for samples under refolding conditions. The broad shoulder that decreases with time is comprised mainly of intermediate-sized aggregates (smaller than those eluting at 5 mm), which do not clearly resolve on this HPLC column.

Increasing reaction times leads to an increase in the size of peaks of aggregated species (eluting at 5.0 mm) and a concomitant decrease in the size of the monomer peak (7.5 mm) (FIG. 3). Similar results are obtained when native gel electrophoresis is used to monitor the time course of aggregation. In both cases, the amount of trimer changes very little with increasing reaction time, presumably because the conditions favor aggregation so strongly.

Quantitation of peak area from HPLC, and radioactive counts per band in native gel electrophoresis show that both methods yield similar levels of monomer, trimer, and aggregate (not shown). Small differences between the aggregate peak and the monomer that form under native PAGE vs. HPLC are likely due to the small buffer variations, such as the inclusion of 0.5 M urea in the HPLC. Because HPLC is substantially faster than native gel electrophoresis (1 h vs. 5 h) and less labor intensive, it is well suited to measure the extent of aggregation on-line during refolding reactions. This capability represents an enormous advantage for those interested in monitoring and controlling protein aggregation in biotechnology, research, and industrial applications.

Example 2

Hydrostatic Pressure Inhibits and Reverses Tailspike Aggregation

Figure 4:
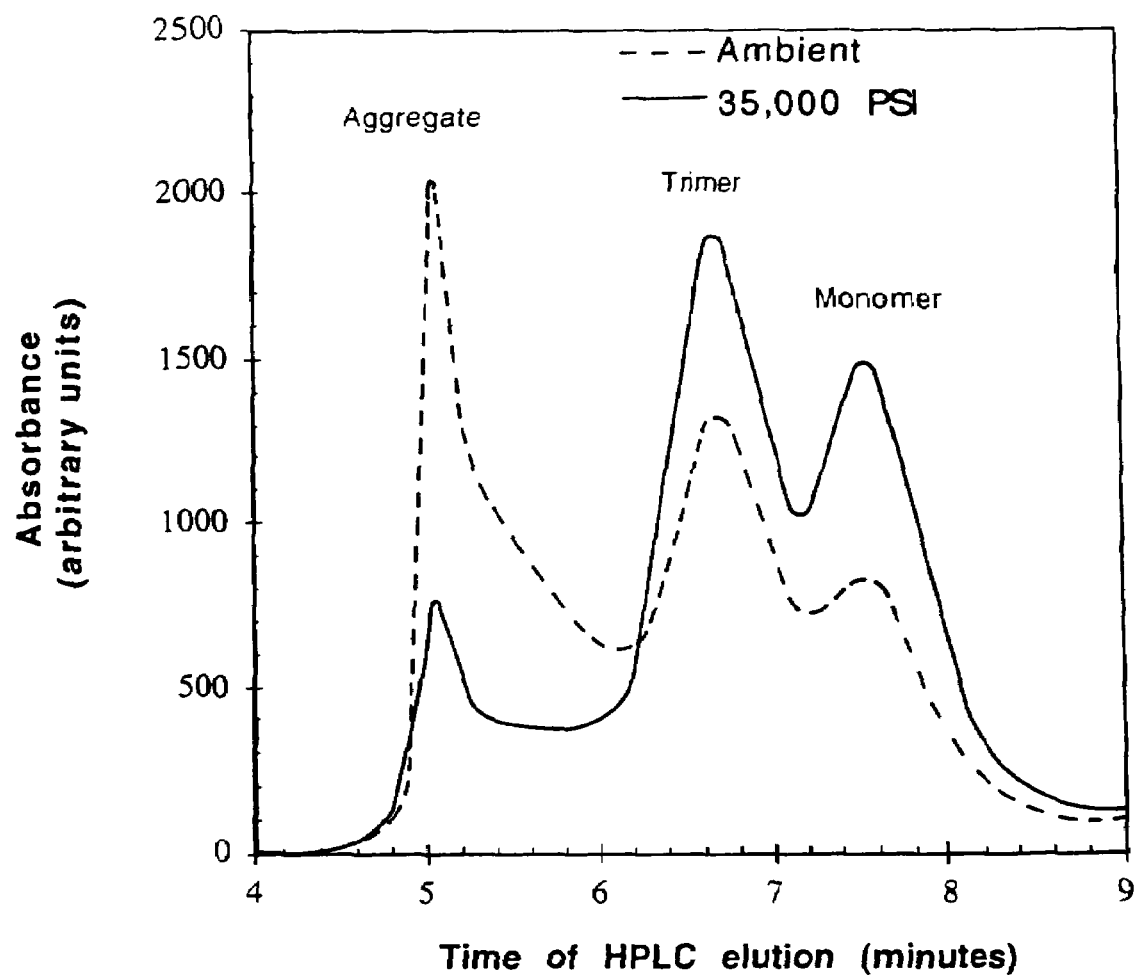
FIG. 4 is a graph showing that tailspike aggregation is reversible under pressure. The graph compares a sample of P22 tailspike protein subjected to high hydrostatic pressure to a control sample held at ambient pressure. The amounts of aggregate, trimer and monomer in each sample are shown.

To test the effect of hydrostatic pressure upon aggregation, samples of native tailspike are denatured, then transferred to refolding buffer under conditions which favor aggregation (t=26° C., [Pt]=1.4 µM chains) and allowed to aggregate for 30 minutes. These samples are termed "ambient aggregated tailspike." An identical set of samples are denatured, transferred to refolding buffer under aggregation conditions, then subjected to 2.4 kbar 90 min, after 3.25 hours of aggregation at atmospheric conditions. These samples are termed "pressure-treated tailspike." For each sample, the extent of refolding and aggregation is analyzed by HPLC (FIG. 4).

Figure 5:
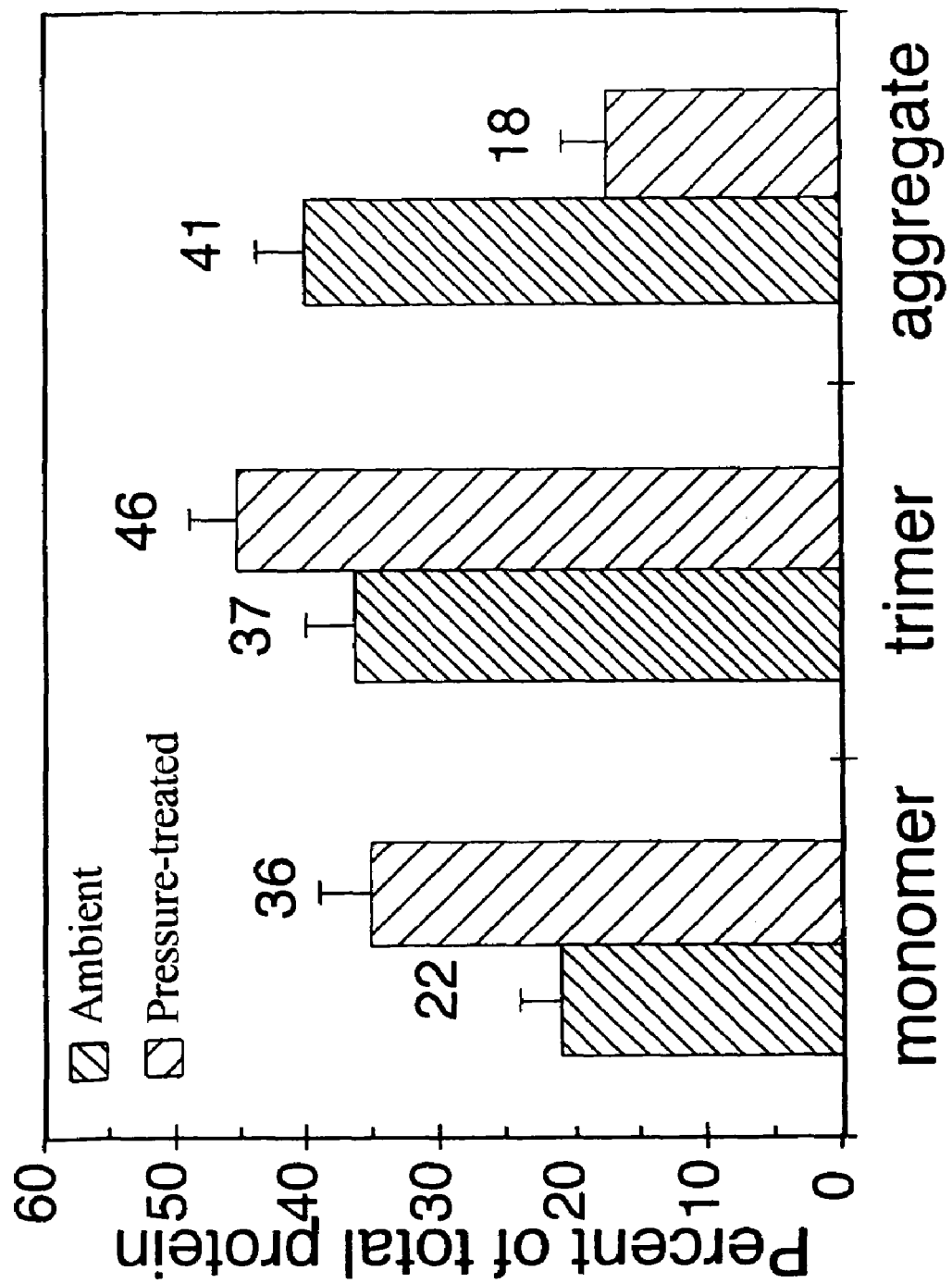
FIG. 5 is bar graph, showing that high hydrostatic pressure rescues native protein from aggregates. Amount of monomer, trimer and aggregate is shown for samples held at ambient pressure (left bar) and samples subjected to high hydrostatic pressure (right bar). Percent of total protein is indicated. Note that the trimer formed, has fluorescence and SDS-resistance similar to that of the native protein. The trimer formed, can also bind to viral heads to form infectious phage.

Treatment with 2.4-kbar hydrostatic pressure markedly increases the yield of native trimer, while substantially decreasing the extent of aggregation. FIG. 5 shows the distribution of tailspike monomers, trimers, and aggregates for pressure-treated tailspike samples and for the ambient aggregated tailspike sample. In the absence of pressure under these conditions, aggregation is favored: Over 40% of the chains are in an aggregated form, with only 22% monomer and 37% trimer after 3.25 hours. In samples incubated at 2.4-kbar for 90 mm, the fractions of trimer and monomer are increased by 25% and 38%, respectively, and the extent of aggregation is decreased by more than 50%.

Example 3

Tailspike Trimers from Pressure Treatment Have Native-Like Structure

Fluorescence Spectroscopy: Fluorescence spectra are recorded using an Hitachi F4500 Spectrofluorometer. All measurements are made at 25° C., in a buffer containing 50 mM sodium phosphate (pH 7.0) and 1 mM EDTA. For all tailspike samples (native, ambient aggregated, and pressure-treated aggregates) the protein concentration is 4 µg/mL. The excitation wavelength is 280 nm, and emission spectra are recorded from 300 to 400 nm. Relative differences in the spectra are determined by determining total peak area as well as the center of mass (average energy of emission).

Results: To demonstrate that tailspike trimers formed from pressure-treated tailspike aggegate recover native-like structural and functional properties, the intrinsic fluorescence spectra and SDS-resistance of native, pressure-treated, and ambient aggregated tailspike are examined.

Tailspike aggregation is accompanied by a large decrease in fluorescence intensity comopared with native tailspike trimers. Pressure treatment of tailspike aggregates produced a 25% increase in fluorescence intensity. This result is consistent with the observation that tailspike trimers in this sample have fluorescence properties similar to native trimers. Pressure-treated and native tailspike trimers also have essentially identical native-gel electrophoretic mobility and size-exclusion HPLC elution times, indicating that their hydrodynamic volume and hydrophobic surface areas are simlar.

Pressure-treated tailspike recover the SDS-resistance characteristic of native tailspike trimers. Incompletely folded tailspike species, including the protrimer, are sensitive to SDS. Pressure treatment of tailspike aggregates produduced a 25% increase in SDS-resistance, which corresponded exactly to the 25% increase in fluorescene in these samples relative to ambient aggregated tailspike. These observations strongly suggest that trimers produced by pressure treatment have native-like secondary and tertiary structure.

Example 4

Tailspike Trimers from Pressure Treatment Have Native-Like Activity

Enzymatic "tailing" Assay: Tail-free heads are prepared from *Salmonella* cells infected with P22 carrying an amber mutation in the tailspike gene, essentially as described in Berget and Poteete, J. Virol. 34:234-243 (1980). Tailspike protein samples are diluted serially 1:3 into M9 media (Sambrook et al., Molecular cloning, a laboratory manual. Cold Spring Harbor, N.Y.: Cold Spring Harbor Laboratory Press (1989)) supplemented with 2 mM $MgSO_4$, to yield a final volume of 100 µL. Then 100 µL aliquots containing $10^9$ tail-free heads are added. Adsorption is allowed to proceed until completion (approximately 4 hours) at room temperature. The reaction mixture is then diluted serially 1:100, and 0.1 mL and 0.5 mL of each dilution are added to two parallel tubes containing 2 mL of top agar (Sambrook et al., 1989) and approximately $2\times10^8$ cells/mL of plating bacteria (*Salmonella* strain 7136) (Israel et al., Proc Natl Acad Sci USA 57:284-291 (1967). This mixture is rapidly mixed and plated onto LB plates and incubated at 37° C. to develop plaques. Plaque formation is the result of lysis of *Salmonella* cells by active P22 virus formed from tailspike protein bound to purified tail-free viral heads. Plaques are counted for dilutions that resulted in 50 to 400 plaques per plate. A control sample containing only tail-free heads is used to measure background phage present; controls containing only tailspike protein are used to determine residual phage in tailspike preps; and a sample of plating bacteria only is used to control for cross-contamination during plating.

Figure 6:
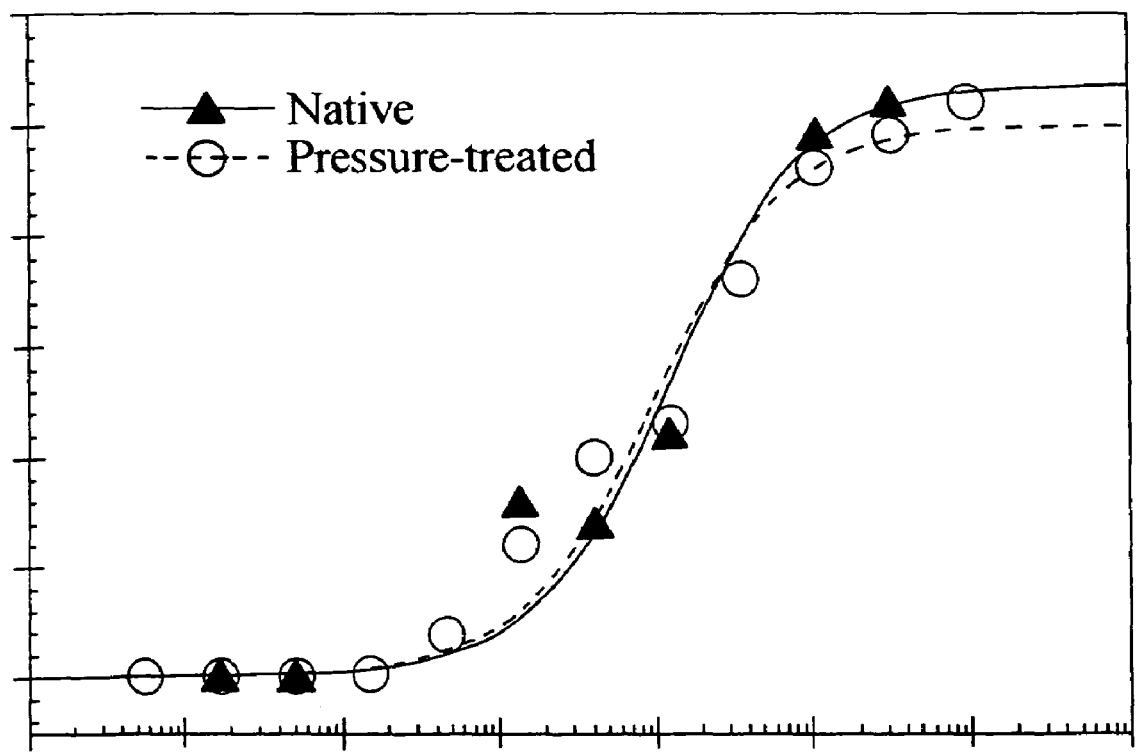
FIG. 6 is a graph showing that pressure-treated tailspike trimers recover native activity. Plaque forming units ($\times 10^7$) are graphed against tailspike concentration ($\mu$g/mL). Pressure-treated tailspike (open circle) is compared with native tailspike trimers (solid triangle) that are not subjected to denaturation or pressure treatment.

Results: To assess whether tailspike trimers produced by pressure-treating aggregates recovered wild-type function, tailspike samples are subjected to the "tailing" assay described above, to determine ability to complement tail-free P22 viral heads and produce infectious viral particles. Samples of native tailspike and pressure-treated aggregates are diluted and incubated with tail-free heads as described. Tailspike trimers produced by pressure treatment of aggregates are essentially fully active, and form viral plaques efficiently. The results are depicted in FIG. 6. The results confirm that refolding under pressure produces tailspike trimers with essentially native structural and functional characteristics.

Example 5

High Pressure Favors Dissociation of Aggregates

In order to determine the effect prolonged exposure to high hydrostatic pressure, tailspike aggregates are formed by allowing tailspike samples to refold under the aggregation conditions, essentially as described in Example 1. Tailspike samples are subjected to hydrostatic pressure of 2.1 kbar for 3 hours. Control samples are held at ambient pressure for the same duration. Upon release of hydrostatic pressure, samples are subjected to native gel electrophoresis, as described in Example 1.

Figure 7:
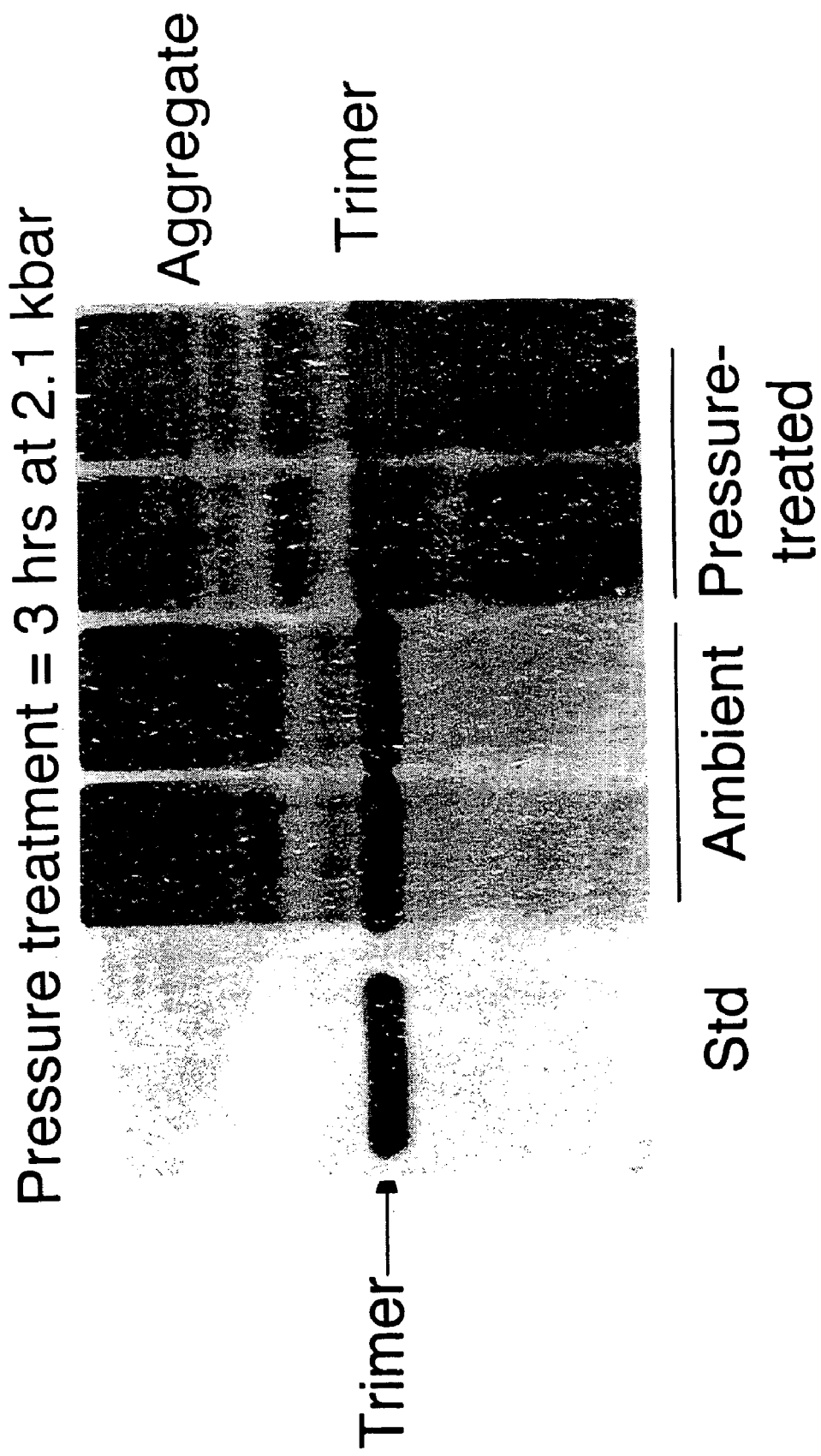
FIG. 7 is a diagram of a non-denaturing gel, showing that high pressure favors dissociation of aggregates. Samples of P22 tailspike protein are either held at ambient pressure or subjected to high hydrostatic pressure (2.1 kbar) for 3 hours, then analyzed by denaturing gel electrophoresis. A known P22 trimer standard is pictured at the left for reference.

The results are depicted in FIG. 7. Lane 1 is a control sample of native trimers. Lanes 4 and 5 are aggregated samples, subjected to high hydrostatic pressure, as described above. Lanes 2 and 3, are samples that are allowed to aggregate under refolding conditions for 3 hours. The results show that there is increased formation of monomer and dimer with exposure to high hydrostatic presure for a extended duration.

Example 6

Pressure Generated Intermediates Are Folding Competent

In order to determine the effect of pressure, tailspike aggregates are formed by allowing tailspike samples to refold under the aggregation conditions, essentially as described in Example 1. After 93 minutes or more of aggregation, samples are subjected to hydrostatic pressure of 35,000 PSI for 90 minutes. Control samples are held at ambient pressure for 93 and 196 minutes. Samples are removed and analyzed by native gel electrophoresis, as described in Example 1.

Figure 8:
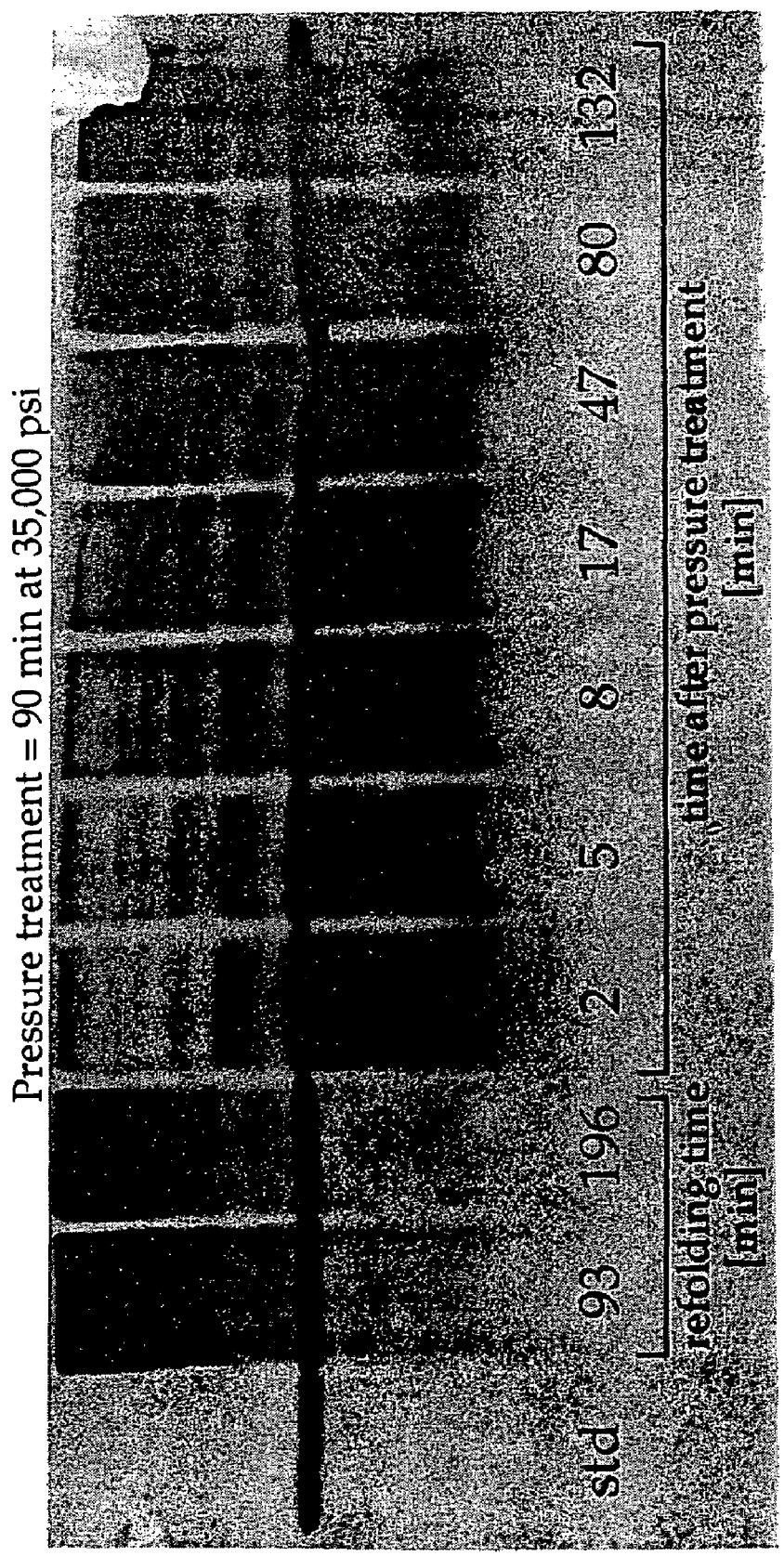
FIG. 8 is a diagram of a non-denaturing gel, showing that intermediates generated by high hydrostatic pressure are folding-competent. Samples of aggregated P22 tailspike protein subjected to high hydrostatic pressure (35,000 psi) for 90 minutes, allowed to refold for 2, 5, 8, 17, 47, 80 and 132 minutes, then analyzed by denaturing gel electrophoresis. A known P22 trimer standard is pictured at the left for reference.

The results are depicted in FIG. 8. Lane 1 is a control sample of native trimers. Lanes 2 and 3, are samples that are allowed to aggregate under refolding conditions for 93 and 196 minutes, respectively. Lanes 3 through 9 are aggregated samples, subjected to high hydrostatic pressure for 90 minutes, at 35,000 psi. At 2, 5, 8, 17, 47, 80 and 132 minutes after pressure treatment, samples are removed and subjected to native gel electrophoresis. The results show that the samples held at ambient pressure are composed primarily of aggregates, with trimer readily identifiable. Samples subjected to 35,000 PSI of hydrostatic pressure, however, shows a marked reduction in the amount of aggregate present.

In contrast to the samples held at ambient pressure, the sample subjected to high hydrostatic pressure is composed primarily of trimers, dimers and monomers. Following the release of pressure, the amount of monomer and dimer present in the pressure treated samples decreases with increasing time. The amount of trimer increases over time, with relatively little formation of aggregates.

Example 7

Dissociation of Transthyetin Fibers by High Hydrostatic Pressure

Dissociati on and denaturation of TTR by high pressure is investigated at pH 7.5 and 5.6 at 37° C. These two pH values approximate conditions found in blood and during cellular processing of proteins in lysosomes. TTR has two tryptophan residues per monomer, located far apart in the tertiary structure. Tryptophan 79 is highly quenched in the tetramer at pH 7, whereas tryptophan 41 makes the major contribution to the fluorescence emission spectrum. High pressure promotes a red shift of the tryptophan emission, resulting in a decrease of the center of spectral mass. After decompression, the, initial center of mass is completely restored, indicating reversibility of the conformational changes induced by pressure.

Reduced temperature facilitates the pressure-induced dissociation and denaturation of several proteins and macromolecular assemblages. The combined effects of high hydrostatic pressure and low temperature on TTR are therefore investigated at pH 5.6. TTR denatures at much lower pressures at 1° C. than at 37° C., demonstrating the entropic character of folding and association of TTR. The $p_{1/2}$ values (pressure that causes 50% denaturation) is 1.9 and 1.3 kbar at 37° C. and 1° C., respectively.

Refolded transthyretin does not aggregate when returned to atmospheric pressure at 1° C. A sample of TTR is subjected to 3.5 kbar at 1° C. for 60 minutes. After return to atmospheric pressure, the sample is maintained on ice and injected into a HPLC-gel filtration column. The control sample at pH 5.6 (not subjected to pressure) elutes as a single peak at approximately 11 min, compatible with a tetramer the size of TTR. After pressure treatment at 1° C., the peak corresponding to the tetramers is again the prominent species, but a new peak eluting around 17.4 min is observed. This peak, approximately 20% of the total protein present after decompression, is compatible with TTR monomers. After 30 min at 1 bar on ice, an aliquot of this same sample is reinjected into the HPLC. The monomer population decreases to less than 10% of the total protein present, whereas the tetramer peak exhibits a small increase, suggesting reassociation of the monomers. It is noteworthy that no monomers are detected when TTR is pressurized at 37° C. and then injected into the HPLC, presumably because of rapid reassociation aided by the high temperature. A monomeric fraction can be detected only when the reassociation is slowed, by keeping the temperature at 1° C.

Example 8

Effect of High Hydrostatic Pressure on p53

The tumoral suppressor p53-DNA binding domain (p53-DBD) is a very unstable protein. Once denatured by high temperature, it aggregates into an apparently amorphous precipitate that cannot be refolded by traditional protein refolding methods. Therefore, the effect of high hydrostatic pressure on the amorphous aggregate of p53-DNA binding domain is investigated. Amorphous p53-DBD aggregate is produced by high temperature precipitation of isolated p53-DBD. The p53-DBD aggregate is then subjected to high hydrostatic pressure, either at reduced temperature (1° C.) or at room temperature, essentially as described in Example 2. When amorphous p53-DBD aggregate is denatured by a combination of pressure and low temperature, it returns back to the native state after removal of high hydrostatic pressure. High hydrostatic pressure at room temperature, however, induces formation of regular aggregate.

What is claimed is:

1. A method for recovering native protein from a sample comprising protein aggregates, said method comprising the steps of:
    (a) obtaining a sample comprising protein aggregates wherein the sample is substantially free of a denaturing agent;
    (b) subjecting the sample of step (a) to elevated hydrostatic pressure, whereby a portion of protein dissociates from said protein aggregates; and
    (c) returning the sample of step (b) to ambient pressure without repeatedly cycling the sample between the elevated and the ambient pressures, whereby a portion of the dissociated protein refolds to native protein.

2. The method of claim 1, wherein said protein aggregates are inclusion bodies.

3. The method of claim 1, wherein said elevated hydrostatic pressure is insufficient to fully denature said protein.

4. The method of claim 1, wherein said sample further comprises a chaotropic agent in an amount which is insufficient to denature said native protein at ambient pressure.

5. The method of claim 4, wherein said elevated hydrostatic pressure is insufficient to fully denature said protein.

6. The method of claim 5, wherein said protein aggregates are inclusion bodies.

* * * * *